US010828387B2

(12) United States Patent
Floyd et al.

(10) Patent No.: US 10,828,387 B2
(45) Date of Patent: Nov. 10, 2020

(54) METHOD OF SEALING A DUROTOMY

(71) Applicant: St. Teresa Medical, Inc., Eagan, MN (US)

(72) Inventors: Timothy Floyd, Eagle, ID (US); Philip A. Messina, Eagan, MN (US)

(73) Assignee: St. Teresa Medical, Inc., Eagan, MN (US)

(*) Notice: Subject to any disclaimer, the term of this patent is extended or adjusted under 35 U.S.C. 154(b) by 0 days.

(21) Appl. No.: 15/293,023

(22) Filed: Oct. 13, 2016

(65) Prior Publication Data

US 2017/0136141 A1 May 18, 2017

Related U.S. Application Data

(60) Provisional application No. 62/254,472, filed on Nov. 12, 2015.

(51) Int. Cl.
A61K 38/36 (2006.01)
A61L 15/44 (2006.01)
A61K 38/48 (2006.01)
A61L 15/28 (2006.01)
A61L 15/38 (2006.01)
A61L 15/64 (2006.01)

(52) U.S. Cl.
CPC ............ *A61L 15/44* (2013.01); *A61K 38/363* (2013.01); *A61K 38/4833* (2013.01); *A61L 15/28* (2013.01); *A61L 15/38* (2013.01); *A61L 15/64* (2013.01); *C12Y 304/21005* (2013.01); *A61L 2300/418* (2013.01); *A61L 2400/04* (2013.01); *A61L 2430/32* (2013.01); *A61L 2430/34* (2013.01); *A61L 2430/36* (2013.01)

(58) Field of Classification Search
None
See application file for complete search history.

(56) References Cited

U.S. PATENT DOCUMENTS

| 4,275,721 | A | | 6/1981 | Olson |
| 4,696,812 | A | | 9/1987 | Silbering |
| 5,447,423 | A | | 9/1995 | Fuisz |
| 5,631,011 | A | | 5/1997 | Wadstrom |
| 5,667,864 | A | | 9/1997 | Landoll |
| 5,702,715 | A | * | 12/1997 | Nikolaychik ....... A61L 24/0073 106/124.5 |
| 5,773,033 | A | | 6/1998 | Cochrum |
| 5,795,571 | A | | 8/1998 | Cederholm-Williams |
| 6,010,627 | A | | 1/2000 | Hood, III |
| 6,054,122 | A | | 4/2000 | MacPhee |
| 6,056,970 | A | | 5/2000 | Greenawalt |
| 6,116,880 | A | | 9/2000 | Bogue |
| 6,117,425 | A | | 9/2000 | MacPhee |
| 6,753,454 | B1 | | 6/2004 | Smith |
| 6,762,336 | B1 | | 7/2004 | MacPhee |
| 6,821,479 | B1 | | 11/2004 | Smith |
| 7,019,191 | B2 | | 3/2006 | Looney |
| 7,067,444 | B2 | | 6/2006 | Luo |
| 7,101,862 | B2 | | 9/2006 | Cochrum |
| 8,580,532 | B2 | | 11/2013 | Ikeda |
| 9,399,082 | B2 | | 7/2016 | Bowlin |
| 9,555,157 | B2 | | 1/2017 | Olson |
| 2002/0022588 | A1 | | 2/2002 | Wilkie |
| 2002/0164322 | A1 | | 11/2002 | Schaufler |
| 2003/0028196 | A1 | | 2/2003 | Bonutti |
| 2003/0168756 | A1 | | 9/2003 | Balkus |
| 2004/0018226 | A1 | | 1/2004 | Wnek |
| 2004/0106617 | A1 | | 6/2004 | Backstrom |
| 2004/0193088 | A1 | | 9/2004 | Looney |
| 2004/0229333 | A1 | | 11/2004 | Bowlin |
| 2005/0186274 | A1 | | 8/2005 | Kohlrausch |
| 2005/0226916 | A1 | | 10/2005 | Cochrum |
| 2005/0245966 | A1 | | 11/2005 | Hammerslag |
| 2005/0284809 | A1 | | 12/2005 | Looney |
| 2006/0002918 | A1 | | 1/2006 | Jiang |
| 2006/0013863 | A1 | | 1/2006 | Shalaby |
| 2006/0141018 | A1 | | 6/2006 | Cochrum |
| 2006/0155235 | A1 | | 7/2006 | Sawyer |
| 2006/0204441 | A1 | | 9/2006 | Atala |
| 2006/0240110 | A1 | | 10/2006 | Kiick |
| 2006/0264130 | A1 | | 11/2006 | Karles |

(Continued)

FOREIGN PATENT DOCUMENTS

CN 101214391 A 7/2008
CN 102258770 A 11/2011

(Continued)

OTHER PUBLICATIONS

Shaffrey ("Neurosurgical Application of Fibrin Glue: Augmentation of Dural Closure in 134 Patients", Neurosurgery, vol. 26, Issue 2, 1990, 207-210) (Year: 1990).*
Ruban ("Management of incidental durotomy in minimally invasive spine surgery", Neurosurgery Focus, 31, (4):E15, 2011), (Year: 2011).*
Merriam-Webster, ("Pledget", definition, provided by www.merriam-webster.com/dictiohary/pledget, pdf captured on Aug. 31, 2018). (Year: 2018).*
International Search Report and Written opinion for PCT App. No. PCT/US2016/056872 dated Dec. 15, 2016, 12 pgs.

(Continued)

Primary Examiner — Robert J Yamasaki
Assistant Examiner — Charles Zoltan Constantine
(74) Attorney, Agent, or Firm — Moss & Barnett; Michael A. Bondi

(57) ABSTRACT

A method of sealing a durotomy from which cerebrospinal fluid is leaking. A durotomy sealant dressing is prepared by applying an active agent to a dextran base. The durotomy sealant dressing is applied to a durotomy. At least a portion of the durotomy sealant dressing dissolves. The durotomy is sealed with the dissolved durotomy sealant dressing to substantially prevent cerebrospinal fluid from flowing through the durotomy.

15 Claims, 2 Drawing Sheets

(56) References Cited

U.S. PATENT DOCUMENTS

| | | |
|---|---|---|
| 2007/0021703 A1 | 1/2007 | McCarthy |
| 2007/0104705 A1 | 5/2007 | Jiang |
| 2007/0160638 A1 | 7/2007 | Mentkow |
| 2007/0160653 A1 | 7/2007 | Fischer |
| 2007/0255238 A1 | 11/2007 | Cochrum |
| 2008/0020015 A1 | 1/2008 | Carpenter |
| 2008/0021545 A1 | 1/2008 | Reneker |
| 2008/0265469 A1 | 10/2008 | Li |
| 2008/0286329 A1 | 11/2008 | Campbell |
| 2009/0053288 A1 | 2/2009 | Eskridge, Jr. |
| 2009/0130186 A1 | 5/2009 | McCarthy |
| 2009/0155342 A1 | 6/2009 | Diegelmann |
| 2009/0177272 A1 | 7/2009 | Abbate |
| 2009/0192214 A1 | 7/2009 | Gravett |
| 2009/0246238 A1 | 10/2009 | Gorman |
| 2009/0291124 A1 | 11/2009 | Bedard |
| 2010/0016802 A1 | 1/2010 | Tambourgi |
| 2010/0100123 A1 | 4/2010 | Bennett |
| 2010/0158989 A1 | 6/2010 | Mentkow |
| 2010/0209392 A1 | 8/2010 | Sista |
| 2010/0247614 A1 | 9/2010 | Jiang |
| 2010/0254900 A1 | 10/2010 | Campbell |
| 2010/0291182 A1 | 11/2010 | Palasis |
| 2011/0021964 A1 | 1/2011 | Larsen |
| 2011/0034410 A1 | 2/2011 | McCarthy |
| 2011/0071498 A1 | 3/2011 | Hakimimehr |
| 2011/0071499 A1 | 3/2011 | Hakimimehr |
| 2011/0111012 A1 | 5/2011 | Pepper |
| 2011/0112572 A1 | 5/2011 | Miller |
| 2011/0125089 A1 | 5/2011 | Senderoff |
| 2011/0150973 A1 | 6/2011 | Bowlin |
| 2011/0171281 A1 | 7/2011 | Cao |
| 2011/0250257 A1 | 10/2011 | Arthur |
| 2012/0128653 A1 | 5/2012 | Goessl |
| 2012/0184891 A1 | 7/2012 | Johannison |
| 2013/0095165 A1 | 4/2013 | Olson |
| 2013/0095229 A1 | 4/2013 | Olson |
| 2013/0096479 A1 | 4/2013 | Olson |
| 2013/0280321 A1 | 10/2013 | Olson |
| 2013/0287837 A1 | 10/2013 | MacPhee |
| 2014/0023714 A1 | 1/2014 | Gagnieu |
| 2014/0205636 A1 | 7/2014 | Ethicon |
| 2014/0220130 A1 | 8/2014 | Larsen et al. |
| 2015/0017225 A1 | 1/2015 | Hubbell |
| 2015/0258239 A1 | 9/2015 | Lamberti et al. |
| 2016/0193381 A1 | 7/2016 | Olson et al. |

FOREIGN PATENT DOCUMENTS

| | | |
|---|---|---|
| CN | 103505758 A | 1/2014 |
| EP | 0693290 A1 | 1/1996 |
| EP | 2441477 A1 | 4/2012 |
| JP | 2000300250 A | 10/2000 |
| JP | 2005290610 A | 10/2005 |
| JP | 2007526026 A | 9/2007 |
| WO | 1999059647 A1 | 11/1999 |
| WO | 2000033744 A1 | 6/2000 |
| WO | 2003/063922 A1 | 8/2003 |
| WO | 2005062880 A2 | 7/2005 |
| WO | 2006088912 A2 | 8/2006 |
| WO | 2006088912 A3 | 8/2006 |
| WO | 2006090150 A1 | 8/2006 |
| WO | 20060119487 A2 | 9/2006 |
| WO | 2006106514 A2 | 10/2006 |
| WO | 2009042829 A1 | 4/2009 |
| WO | 2009126870 A2 | 10/2009 |
| WO | 2010002435 A2 | 1/2010 |
| WO | 2010002435 A3 | 1/2010 |
| WO | 2013059346 A1 | 4/2013 |

OTHER PUBLICATIONS

Stephen W. Rothwell, et al., A Salmon Thrombin-Fibrin Bandage Controls Arterial Bleeding in a Swine Aortotomy Model, The Journal of TRAUMA, Jul. 1, 2005, pp. 143-149, vol. 59 No. 1.

Jiang et al., Optimization and Characterization of Dextran Membranes Prepared by Electrospinning, Biomacromolecules, 5(2):326-333 (Mar.-Apr. 2004).

Jiang et al., "Modulation of Protein Release from Biodegradable Core-Shell Structured Fibers Prepared by Coaxial Electrospinning", Journal of Biomedical Materials Research Part B: Applied Biomaterials, 79B(1):50-57 (Oct. 2006).

Schanbacher, Anticoagulants and Blood Thinners during Cutaneous Surgery: Always Cometime or Never? Skin Therapy Letter 2004; 9(3).

Kagoma et al., Use of Antifibrinolytic Therapy to Reduce Transfusion in Patients Undergoing Orthopedic Surgery: A Systematic Review of Randomized Trials.

America Family Physician, Cuts, Scrapes and Stitches, Am Fam Physician. Jun. 1, 2004;69(11): 2647-2648.

Bowles et al., Wound Microbiology and Associated Approaches to Wound Management, Clinical Microbiology Reviews, Apr. 2001, p. 244-269.

Sigma-Aldrich, "BIS-TRIS," Specification Comparison, Sigma-Aldrich Co., 2 pages, available at https://www.sigmaaldrich.com/content/dam/sigma-Aldrich/Datasheet/bis-tris_specification_chart.pdf (Year: 2010).

Kumar et al., "Whole Blood Thrombin: Development of a Process for Intra-Operative Production of Human Thrombin," The Journal of the American Society of Extra-Corporeal Technology, vol. 39, No. 1, pp. 18-23 (Year 2007).

Stephen W. Rothwell et al., "The Long Term Immunilogical Response of Swine after Two Exposures to a Salmon Thrombin and Fibrinogen Hemostatic Bandage", Biologicals, vol. 38, No. 6, Nov. 1, 2010, pp. 619-628, XP055178774, ISSN: 1045-1056, DOI: 10.1016/j.biologicals.2010.07.001.

International Preliminary Report on Patentability for PCT Application No. PCT/US2016/056872; dated May 24, 2018, 8 pgs.

Database WPI Week 201203 Thomson Scientific, London, GB; An 2011-Q86545 XP002783017 & CN102258770 A (Shanghai Likangrui Biological Eng Co Ltd), Nov. 30, 2011, 2 pgs.

Stephen W. Rothwell et al., "Wound healing and the immune response in swine treated with a hemostatic bandage composed of salmon thrombin and fibrinogen", Journal of Materials Science: Materials in Medicine, Kluwer Academic Publishers, BO, vol. 20, No. 10, May 18, 2009 (May 18, 2009), pp. 2155-2166, X019750141, ISSN: 1573-4838, DOI: 10.1007/S10856-009-3769-2.

Shaffrey, "Neurosurgical Application of Fibrin Glue: Augmentaton of Dural Closure in 134 Patients", Neurosurgery, vol. 26, Issue 2, 1990, 207-210, 4 pgs.

Ruban, "Management of Incidental Durotomy in Minimally Invasive Spine Surgery", Neurosurgery Focus, 31, (4):E15, 2011, 6 pgs.

Merriam-Webster, "Pledglet", definition, provided by www.merriam-webster.com/dictionary/pledglet, pdf captured on Aug. 31, 2018, 3 pgs.

Extended European Search Report and Written Opinion received in EP. Serial No. 16864740.2, Jun. 6, 2019, 9 pgs.

Stryker Orthopaedics, Triathlon Knee System Surgical Protocol, 2015, 29 pgs.

Lu et al., Perioperative Blood Management Strategies for Total Knee Anthroplasty, Orthopedic Surgery, vol. 10, No. 1, Feb. 2018, 9 pgs.

* cited by examiner

METHOD OF SEALING A DUROTOMY

REFERENCE TO RELATED APPLICATION

This application claims priority to Provisional Applic. No. 62/254,472, filed on Nov. 12, 2015, the contents of which are incorporated herein by reference.

FIELD OF THE INVENTION

The invention relates to methods of sealing biological fluids. More particularly, the invention relates to methods of sealing a durotomy using a durotomy sealant dressing to prevent leakage of cerebrospinal fluid.

BACKGROUND OF THE INVENTION

The dura mater is located between the cranium and the brain and around the spinal cord. The principal function of the dura mater is to protect the brain and spinal cord and prevent leakage of cerebrospinal fluid.

It is possible for the dura mater to become unintentionally or intentionally perforated. Unintentional perforation of the dura mater may occur from a traumatic event like an automobile accident. Intentional dura mater perforation can occur when performing certain surgical procedures, such as to provide access to the brain, spinal cord or other structures within the central nervous system.

In both of these situations, it is important to quickly and reliably seal the dura mater to minimize the loss of cerebrospinal fluid as the cerebrospinal fluid plays a critical role in supporting the brain in the cranium and the body has a limited ability at which cerebrospinal fluid can be produced to replace the cerebrospinal fluid that is lost. If the loss of cerebrospinal fluid is not quickly stopped, the patient may experience serious health complications and possibly death.

SUMMARY OF THE INVENTION

An embodiment of the invention is directed to a method of sealing a durotomy from which cerebrospinal fluid is leaking. A durotomy sealant dressing is prepared by applying an active agent to a dextran base. The durotomy sealant dressing is applied to a durotomy. At least a portion of the durotomy sealant dressing dissolves. The durotomy is sealed with the dissolved durotomy sealant dressing to substantially prevent cerebrospinal fluid from flowing through the durotomy.

Another embodiment of the invention is directed to a method of sealing a durotomy from which cerebrospinal fluid is leaking. A durotomy sealant dressing is prepared by applying an effective amount of thrombin and an effective amount of fibrinogen to an electrospun dextran fiber base. The durotomy sealant dressing is applied to a durotomy. At least a portion of the durotomy sealant dressing dissolves. The durotomy is sealed with the dissolved durotomy sealant dressing to substantially prevent cerebrospinal fluid from flowing through the durotomy.

Another embodiment of the invention is directed to a method of sealing a durotomy from which cerebrospinal fluid is leaking. A durotomy sealant dressing is prepared by applying an active agent to a dextran base. The durotomy sealant dressing is applied to a durotomy. A liquid is applied to the durotomy sealant dressing. At least a portion of the durotomy sealant dressing dissolves. The durotomy is sealed with the dissolved durotomy sealant dressing to substantially prevent cerebrospinal fluid from flowing through the durotomy.

BRIEF DESCRIPTION OF THE DRAWINGS

The accompanying drawings are included to provide a further understanding of embodiments and are incorporated in and constitute a part of this specification. The drawings illustrate embodiments and together with the description serve to explain principles of embodiments. Other embodiments and many of the intended advantages of embodiments will be readily appreciated as they become better understood by reference to the following detailed description. The elements of the drawings are not necessarily to scale relative to each other. Like reference numerals designate corresponding similar parts.

DETAILED DESCRIPTION OF THE INVENTION

Figure 1:
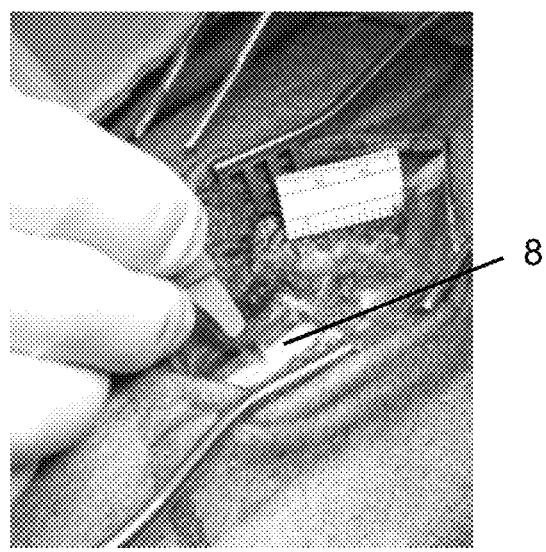
FIG. 1 is a photograph showing forming an incision in dura mater.

An embodiment of the invention is directed to a system and method for sealing a durotomy using a durotomy sealant dressing. Sealing the durotomy thereby prevents cerebrospinal fluid leaking from the durotomy. It is possible for the durotomy to be formed by a variety of causes such as intentionally with an incision while performing a surgical procedure or unintentionally from a traumatic event such as an automobile accident.

The components used in fabricating the durotomy sealant dressing should be selected to be the same as components found in a living body where the durotomy sealant dressing is to be used. Alternatively, the components used in fabricating the durotomy sealant dressing are compatible with and readily broken down when the durotomy sealant dressing is used in a living body.

Using such a process minimizes complications associated with components of the durotomy sealant dressing not being promptly being broken down as such a process could cause inflammation in the living body. The only residual material after the use of the durotomy sealant dressing is a mass formed when the durotomy sealant dressing encounters fluid such as cerebrospinal fluid, which most living bodies are adapted to degrade over time.

The invention generally includes a durotomy sealant dressing having a base to which at least one active agent is associated. In certain embodiments, the base is fabricated from electrospun dextran.

Electrospinning is a non-mechanical processing strategy and can be scaled to accommodate the large volumes necessary to meet the needs of commercial processing. Additional details on the electrospinning process are provided in U.S. application Ser. No. 12/937,322, the contents of which are incorporated herein by reference.

In certain embodiments, the base used in the durotomy sealant dressing is formed of substantially homogeneous spun dextran. As used herein, homogeneous means that there are typically no additional components other than the solvent in the electrospun dextran fibers. The amount of dextran used in each durotomy sealant dressing can vary depending on the size of durotomy sealant dressing that is being manufactured and the size of the durotomy sealant dressing may be selected based upon at least one of the size of the durotomy and the rate at which cerebrospinal fluid is flowing from the durotomy. In certain embodiment, there is between about 0.2-10 grams of dextran (usually 100,000-200,000 Mr) per durotomy sealant dressing.

Of more consequence is the concentration of dextran in the solution from which the fibers are electrospun. Generally, a solution of dextran for electrospinning will be of a concentration in the range of between about 0.1 and about 10 grams per milliliter of solvent. In other embodiments, the dextran concentration is between about 0.5 and about 5 grams per milliliter of solvent, and usually such a solution is at a concentration of about 1 gram per milliliter of solvent, which is about 0.15 milligrams. A preferred range would be from about 0.9 to about 1.1 grams of dextran per milliliter of solvent that is to be electrospun.

The area (length and width) of the durotomy sealant dressing of the invention can vary and be adjusted by adjusting spinning parameters. In addition, the mats of dextran fibers can be cut to a desired size after spinning. Generally, the durotomy sealant dressing will be from about 0.5 centimeters or less to about 30 centimeters or more in length and/or width, but larger or smaller sizes are also contemplated depending on the intended use of the durotomy sealant dressing.

Those of skill in the art will recognize that a variety of liquid solvents exist in which it is possible to dissolve dextran. However, superior results for electrospinning dextran are generally achieved when the solvent is water, especially deionized or distilled or deionized, distilled (ddH2O) or other forms of relatively pure water. In addition, there are no negative interactions during use of the durotomy sealant dressing associated with water remaining in the durotomy sealant dressing and there is far less environmental impact associated with the use of water as compared to many other solvents.

The bioactive agents have a beneficial or therapeutic effect at the durotomy site. In one embodiment, the site is the location of a puncture or incision formed in the dura mater. In this embodiment, the therapeutic substances of interest may include at least one of thrombin and fibrinogen, although other agents active in stopping the flow of cerebrospinal fluid may also be included.

The thrombin and/or fibrinogen that are used in the durotomy sealant dressing are in forms that are biologically active when they come into contact with cerebrospinal fluid. Hence upon dissolution of the electrospun dextran base, the thrombin acts on the fibrinogen, converting it to fibrin, which then forms a mass at the durotomy site to thereby stop the flow of cerebrospinal fluid.

In certain embodiments, the thrombin and fibrinogen may be derived from human sources. In other embodiments, the thrombin and fibrinogen are salmon thrombin and fibrinogen. Advantages of using salmon as a source of these materials include but are not limited to the lack of concern about transmission of etiologic agents (e.g. viruses) that may occur when human and other mammalian sources of thrombin or fibrinogen (e.g. bovine) are used.

The quantity of fibrinogen added to the durotomy sealant dressing may be adjusted by changing either the concentration of the fibrinogen in the additive mixture or changing the rate at which the additive mixture is used in the durotomy sealant dressing. The quantity of fibrinogen added to the durotomy sealant dressing is generally in the range of from about 10 milligrams to about 3 grams. In certain embodiments, the amount of fibrinogen in each of the durotomy sealant dressings is between about 20 milligrams to about 1 gram.

The quantity of thrombin added to the durotomy sealant dressing may be adjusted by changing either the concentration of the thrombin in the additive mixture or changing the rate at which the additive mixture is used in the durotomy sealant dressing. The quantity of thrombin added to the durotomy sealant dressing is generally between about 10 and 10,000 NIH Units. In certain embodiments, the amount of thrombin in each of the durotomy sealant dressings is between about 20 and 6,000 NIH Units.

Association of active agents with the electrospun dextran base may be accomplished by any of many suitable techniques that are known to those of skill in the art, and will depend in part on the precise form of the substance and the means at hand. For example, for powdered, particulate thrombin and fibrinogen, association may be carried out by sprinkling, shaking, blowing, etc. the agents onto a layer of the excipient or carrier.

In some embodiments, active agents such as thrombin may be electrosprayed with sucrose to form sugar droplets, which tends to stabilize thrombin and can also "trap" other substances of interest for delivery to the durotomy sealant dressing. In other embodiments, the therapeutic agents may themselves be electrospun. For example, the therapeutic agents are dissolved in and electrospun from a solution. The active agents may be electrospun into other forms such as droplets, beads, etc.

In addition, electrospun or non-electrospun collagen, agents that absorb water, various dry salts that would tend to absorb fluids when placed in contact with e.g. cerebrospinal fluid; blood; engineered thrombin or thrombin mimics; engineered fibrinogen; agents that cause vasospasm (e.g. ADP, 5-hydroxytryptamine, 5-HT and thromboxane, (TXA-2) to help contract and seal a bleeding vessel, etc. may also be included.

Other components may be added to the durotomy sealant dressing, for example: tissue factors that are normally only expressed on the surface of damaged cells and that start the normal clotting cascade; serotonin which enhances platelet clumping and promotes vessel constriction; and other agents that are used to replace missing components of the clotting cascade in hemophilia, for example, factor 7 (which activates the so called external extrinsic coagulation cascade) and crude extracts of platelets.

Active agents that function to promote late stages of wound healing may also be included to, for example, facilitate cell migration and remodeling. The incorporation of collagen is an example of such an active agent.

The therapeutic agents must be amenable to drying and are associated with the other components of the durotomy sealant dressing in the dry state, since liquid may negatively affect at least one of the components used in the durotomy sealant dressing. For example, the active agents may be desiccated or lyophilized, or water may be removed by other means.

In certain embodiments, the electrospun dextran base is placed on a vacuum table, which not only retains the electrospun dextran base in a substantially stationary position during the fabrication process but also causes the active agents to be drawn into the electrospun dextran base. This process thereby reduces the potential of the active agent becoming disassociated from the electrospun dextran base while stored in a package as well as when removed from the package prior to applying to the durotomy.

Depending on the density of the fiber mat, the substances of interest may become relatively evenly dispersed throughout the fiber mat or may be largely confined to the topmost section of the fiber mat. If no backing is present, the latter embodiment is preferable to prevent the particulate substance of interest from falling through and out of the fiber mat.

In another embodiment, a first layer of electrospun dextran may be formed, and one or more of the substances may be associated with the first layer. Then a second layer of electrospun dextran may be formed or placed on top of the substance(s) of interest, and the same or other substances of interest may be associated with the second layer, and so on.

A final or outermost layer of electrospun dextran may be added to prevent the dislodgement of substances of interest from the preceding layer. The number of layers of electrospun dextran that are used in the durotomy sealant dressing of the invention may vary widely, from as few as 1-2 to as many as several dozen, or even several hundred, depending on the desired characteristics of the durotomy sealant dressing.

Typically, a durotomy sealant dressing will contain 1-2 layers. In other embodiments the durotomy sealant dressing may include between 2-20 layers. The very slight amount of moisture that is present in a prepared durotomy sealant dressing may help to trap and retain the thrombin and fibrinogen on the surface of the durotomy sealant dressing.

The height or thickness of the durotomy sealant dressing can vary considerably depending on the intended use of the durotomy sealant dressing. In certain embodiments, the durotomy sealant dressing has a thickness of between about 1 millimeter and about 5 centimeters.

The thickness of the durotomy sealant dressing (which is related to the volume) may impact the rate of dissolution of the dextran upon contact with liquid. For example, a thin durotomy sealant dressing (e.g. about 2 millimeters) will dissolve more rapidly than a durotomy sealant dressing that is thicker, providing the loft (density) of the fibers is comparable.

In most embodiments, dissolution of the dextran fibers is extremely rapid, e.g. about 5 minutes or less after exposure to liquid, or about 4 minutes or less, or about 3 minutes or less, or about 2 minutes or less, or about 1 minute or less. In certain embodiments, the durotomy sealant dressing substantially dissolves in between about 1 second and about 20 seconds.

This rapid dissolution may be referred to herein as "instantaneous" or "immediate" dissolution. Compression of an electrospun dextran mat may be used to modulate the rate of dissolution, with greater levels of compression inversely impacting the rate, i.e. generally, the greater the degree of compression, the slower the rate of dissolution.

The rapid rate of dissolution is advantageous, particularly when delivering biologically active agents to a site of action such as a durotomy. Rapid dissolution of the carrier dextran fibers provides extremely rapid delivery of the active agents to the durotomy upon deployment of the durotomy sealant dressing.

Generally, the amount of water that is present in the substances when they are associated with the electrospun dextran fibers is less than about 5%, and preferably less than about 2%. These substances retain full or partial activity when rehydrated, e.g. in cerebrospinal fluid. Generally, therapeutic substances associated with the durotomy sealant dressings of the invention retain, upon contact with liquid, at least about 25%, or about 50%, or even about 75% to 100% of their activity before drying or desiccation, as compared to standard preparations of the substance using standard assays that are known to those of skill in the art.

If thrombin is included in the durotomy sealant dressing, it may be desirable to reduce the moisture content of the durotomy sealant dressing to less than about 5% to preserve thrombin activity during sterilization. This moisture content reduction can be achieved by drying the fabricated durotomy sealant dressing, e.g., under a vacuum, or by using a fabrication method that reduces moisture content from the beginning.

To minimize the potential of degradation of the durotomy sealant dressing, the durotomy sealant dressing should be protected from exposure to moisture because when the components used in the durotomy sealant dressing are exposed to moisture, the components degrade such as by dissolving.

The durotomy sealant dressing may include one or more stabilizers such as is described in U.S. application Ser. No. 13/622,690, which is assigned to the assignee of the present application and the contents of which are incorporated herein by reference. The stabilizers may enhance the ability of the durotomy sealant dressing to dissolve when the durotomy sealant dressings are applied to the durotomy site.

In certain embodiments, the durotomy sealant dressing should resist degradation when exposed to the elevated temperature such as up to about 150° F. for more than about 3 hours. In other embodiments, the durotomy sealant dressing should resist degradation when exposed to the elevated temperature for up to about 24 hours.

A threshold for the durotomy sealant dressing to be viewed as not experiencing degradation is that the durotomy sealant dressing does not exhibit noticeable visible physical changes when viewing the durotomy sealant dressing without magnification. The durotomy sealant dressing should also not experience noticeable physical changes when the durotomy sealant dressing is examined with magnification such as with a magnifying glass or a microscope.

The preceding characteristics should be displayed by the durotomy sealant dressing regardless of whether the durotomy sealant dressing is retained in the packaging materials while exposed to the elevated temperature conditions.

The stabilizer also enhances the usable shelf life of the durotomy sealant dressing. In certain embodiments, the stabilizer provides the durotomy sealant dressing with a shelf life of at least about 2 years. In other embodiments, the durotomy sealant dressing exhibits a shelf life of at least 3 years. As used herein, the term usable shelf life means that the durotomy sealant dressing does not exhibit noticeable degradation when viewed without magnification or with magnification such as a magnifying glass or microscope.

In some embodiments of the invention, the durotomy sealant dressings also include one or more support structures or support materials incorporated therein. For example, a backing may be incorporated into the durotomy sealant dressing.

The support material may be formed from various electrospun materials such as polyglycolic acid (PGA), polylactic acid (PLA), and their copolymers (PLGAs); charged nylon, etc. In one embodiment, the support material is compressed electrospun dextran fibers. By "compressed electrospun dextran fibers," it is meant that electrospun dextran fibers are compressed together under pressure.

The support material may or may not be soluble in liquid, or may be slowly soluble in liquid, and may or may not be permeable to liquid. Slowly soluble materials include those from which absorbable or dissolving (biodegradable) stitches or sutures are formed, included PGA, polylactic and caprolactone polymers.

In certain embodiments, the support material may dissolve relatively quickly such as less than about 1 hour. In other embodiments, the support material may dissolve within from about 10 days to 8 weeks. In either case, the support material provides the advantage of not having to remove the durotomy sealant dressing and risk disrupting the seal at the durotomy site.

However, in any case, the support material should not interfere with the immediate dissolution of the durotomy sealant dressing and delivery of the active agents associated therewith into the liquid that dissolves the durotomy sealant dressing.

All such arrangements, shapes, and embodiments of carrier layers and support materials as described herein are intended to be encompassed by the invention.

The durotomy sealant dressing may be sterilized prior to use, generally by using electromagnetic radiation, for example, X-rays, gamma rays, ultraviolet light, etc. Typically, the durotomy sealant dressings are sterilized using X-rays in a dose of at least about 5 kilograys. Any method that does not destroy the carrier or the activity of substances associated with the fibers may be used to sterilize the durotomy sealant dressings of the invention.

The durotomy sealant dressing may also include diagnostic agents that can be used by the treating medical professional to diagnose the nature of the injury. In certain embodiments, the diagnostic agent may change colors to indicate the presence of particular chemicals in the cerebrospinal fluid or to indicate particular characteristics of the cerebrospinal fluid.

In other embodiments, the products of the invention may also include agents that exhibit additional functionality. Such substances may include, for example, enzymes or their precursors (e.g. pro-enzymes or zymogens) and their substrates, substances that activate a protein or enzyme (e.g. proteases, cofactors, etc.), and the like.

For example, durotomy sealant dressing comprised of only thrombin might be used for small durotomies. In addition, other therapeutically beneficial substances may also be associated with the durotomy sealant dressing, including but not limited to: antibiotics, antiviral agents, anti-helminthic agents, anti-fungal agents, medicaments that alleviate pain, growth factors, bone morphogenic protein, vasoactive materials (e.g. substances that cause vasospasms), steroids to reduce inflammation, chemotherapy agents, etc.

In some embodiments, no cerebrospinal fluid is present (or if insufficient cerebrospinal fluid is present) and the applied durotomy sealant dressing can be "activated" by wetting, e.g. by spraying, or by otherwise applying a source of moisture (e.g. by exposing the durotomy sealant dressing to a moist material such as a sponge), or immersing durotomy sealant dressings in a liquid (e.g. water), to cause release of the agents of interest associated with the dextran fibers.

One of the challenges in successfully treating a durotomy, especially a durotomy where there is significant cerebrospinal fluid flow, is to achieve a seal. In addition to applying the durotomy sealant dressing such as is described in the other portions of this patent application, pressure may be applied to the durotomy to enhance the likelihood that seal will be achieved. Depending on the size and/or shape of the opening through which the cerebrospinal fluid is flowing, it is possible to use at least one suture to approximate the durotomy prior to applying the durotomy sealant dressing.

In certain embodiments, the pressure is provided by direct manual pressure such as using a human hand. In other embodiments, a material such as a pledget is placed over the durotomy and the direct manual pressure is used to hold the durotomy sealant dressing in place. At least a portion of the pledget may be fabricated from a radiopaque material. The pledget may also include a retrieval string that extends therefrom. The retrieval string may be fabricated from with a length that is sufficiently long so that the retrieval string extends outside of the region in which the patient where the durotomy sealant dressing is used. The retrieval string may also be fabricated with a color that contrasts from the colors typically present proximate to where the durotomy sealant dressing is used.

The material may have absorbent capabilities such that cerebrospinal fluid and other fluids that are in proximity to the material are absorbed into the material. In such situations, it is possible for the seal to become associated with the material such as on the surface of the material or at least partially in the matrix of the material.

As the pressure that is applied either solely with manual force or in conjunction with the additional material is removed, it is important to minimize disruption of the seal that caused the cerebrospinal fluid to stop flowing. Such disruption can cause cerebrospinal fluid to resume flowing from the dura mater.

Separation of the material used to apply the pressure from the durotomy area is complicated by the fact that especially when just formed, the seal can be relatively sticky. Additionally, the components used in the durotomy sealant dressings described herein such as thrombin and fibrinogen can also be relatively sticky after being dissolved by contact with a liquid such as cerebrospinal fluid.

The ability to achieve the seal through the use of applying pressure and the ability to separate the object used to apply the pressure from the area in which the seal has been achieved may be enhanced by the use of a hydrogel product intermediate the object used to apply the pressure and the area in which it is desired to achieve the seal.

In addition to the preceding hydrogel components, the hydrogel sheet may include a reinforcing material that increases the structural integrity of the hydrogel sheet and thereby enhances the ability to manipulate the hydrogel sheet without damage thereto such as portions of the hydrogel sheet becoming dislodged.

In certain embodiments, the reinforcing material has a mesh configuration with a plurality of openings formed therein. The openings enables hydrogel placed on opposite sides of the reinforcing material to join together through the reinforcing material. An example of one such hydrogel material is a nylon scrim.

In other embodiments, the reinforcing material is a backing material that is attached to a side of the hydrogel sheet that is opposite the durotomy. To enhance the ability of the hydrogel sheet to remain in attachment with the reinforcing material, the backing material may include pores that are adapted to receive the hydrogel. These pores may be similar to the openings discussed in the preceding paragraph. However, a difference between the reinforcing material discussed in the preceding paragraph and the backing material discussed in this paragraph is that the hydrogel material cannot be contacted on the side of the backing material that is opposite the hydrogel sheet that is in contact with the durotomy.

The backing material may include features that assist in identifying the location of the hydrogel pad. These features also encourage persons who are treating the person with the durotomy to remember to remove the hydrogel pad after an appropriate period of time.

In certain embodiments, the backing material may be formed with a color that contrasts from the color of the person's skin as well as the color of cerebrospinal fluid. For example, the backing material may be formed with a green or blue color.

Alternatively or additionally, the backing material includes a design printed thereon that enhances the ability to identify the location of the hydrogel layer. An example of the design is a plurality of lines that are arranged in an array such as diamonds or squares. The design may be provided in a color that enhances the ability to see this design that thereby identifies the backing material and the associated hydrogel layer.

Alternatively or additionally, the backing material includes text that advises the person applying the hydrogel sheet to remove the hydrogel sheet. Depending on the intended use of the hydrogel sheet, the text may be a general warning or may provide a specific duration in which the hydrogel sheet is to remain on the durotomy.

In the embodiment of the hydrogel sheet that includes the reinforcing material at an intermediate location thereof, a release layer may be provided over the surface of the hydrogel sheet that is opposite the side of the hydrogel sheet that is in contact with the durotomy.

An applicator may be used in conjunction with the hydrogel sheets. The applicator may have an elongated configuration that enables a portion of the applicator to extend outside of a patient's body when in use. The applicator may be fabricated from a relatively rigid material such as plastic.

A portion of the applicator to which the hydrogel sheet is attached may be shaped to generally correspond to the shape of the surface to which the durotomy sealant dressing is intended to be applied. In certain embodiments, the portion of the applicator to which the hydrogel sheet is attached may have a semi-circular shape similar to the shape of a portion of the spine over which the durotomy sealant dressing is applied.

The portion of the applicator to which the hydrogel sheet is attached may have a length and a width that are selected based upon on the length and the width of the durotomy sealant dressing. In certain embodiments, the length and the width of the portion of the applicator to which the hydrogel sheet is attached are approximately the same as the length and the width as the durotomy sealant dressing.

In use, the durotomy sealant dressing is applied to the durotomy and then the pledget is placed over the durotomy sealant dressing. Pressure is applied to the pledget and such pressure causes the durotomy sealant dressing to engage the durotomy for a period of time to promote forming the seal. In certain embodiments, the period of time is up to about 5 minutes. In other embodiments, the period of time is between about 2 minutes and about 3 minutes.

During the time in which the pledget is placed over the durotomy, at least a portion of the durotomy sealant dressing dissolves into and/or around the durotomy. Dissolving causes the components in the durotomy sealant dressing such as thrombin and fibrinogen to be released into the durotomy and thereby cause the seal to be formed.

Thereafter, the pledget is removed from over the durotomy. In certain situations, substantially all of the durotomy sealant dressing has dissolved by the time the pledget is removed from the durotomy. In other situations, a portion of the durotomy sealant dressing remains undissolved when the pledget is removed from the durotomy.

The durotomy is then reviewed to determine if a sufficiently strong seal has been achieved. If a sufficiently strong seal has not been achieved, the pledget is placed over the durotomy. Pressure is applied to the pledget for an additional period of time. In certain embodiments, the additional period of time is up to about 5 minutes. In other embodiments, the additional period of time is between about 2 minutes and about 3 minutes.

In other embodiments where leakage of cerebrospinal fluid is significant after the pledget is removed and a substantial portion of the durotomy sealant dressing has dissolved, another durotomy sealant dressing is placed over the durotomy prior to the pledget being reapplied on the durotomy. This process can be repeated until a sufficiently strong seal has been achieved.

Each time the pledget is separated from the durotomy, the at least partially solidified components in the durotomy such as the undissolved portions of the durotomy sealant dressing remain associated with the durotomy instead of being associated with the pledget such that separation of the pledget from the durotomy does not cause such materials to be pulled away from the durotomy by the pledget.

The pledget can include a radiopaque marker that can be used to determine if the pledget using an imaging technique such as x-ray imaging. The radiopaque marker may be incorporated into or otherwise associated with the pledget.

In addition to being used to produce a durotomy seal in humans, the concepts of the invention may be adapted for use in conjunction with other animals. Examples of such animals on which the invention can be used include dogs and cats.

The product and method of the present invention are described in the following examples. These examples are provided as an illustration of the invention and are not intended to limit the invention.

Example 1

Dextran is mixed with an effective amount of water to form an aqueous dextran solution. The aqueous dextran solution is electrospun to form an electrospun dextran sheet.

Thrombin and fibrinogen were mixed together and then dispersed on the electrospun dextran sheet. The thrombin was dispensed at a rate of between about 1.3 and 2.7 NIH Units per square centimeter of the electrospun dextran sheet. The fibrinogen was dispensed at a rate of between about 3.6 and 7.4 milligrams per square centimeter of the electrospun dextran sheet.

This process was repeated until there were 3 layers of the electrospun dextran sheet in a stacked configuration. The thrombin and fibrinogen mixture was not dispersed on the surface of the uppermost layer. The electrospun dextran sheet has a thickness of between about 1 and 3 millimeters.

A cutter was then used to cut the durotomy sealant dressing into pieces having a width of about 3.2 centimeters and a length of about 3.2 centimeters. Each of the durotomy sealant dressings had a dextran weight of between about 0.20 grams and about 0.40 grams. In addition to forming pieces of a desired size, the cutting causes the electrospun dextran layers to be pushed together. This process caused the electrospun dextran layers to resist separation. The pieces of the durotomy sealant dressings were vacuum packaged for storage until use. In addition to preventing contamination of the durotomy sealant dressing, the vacuum packaging caused the layers of the electrospun dextran to be urged together.

Example 2

Five adult goats were used in this study that was performed pursuant to good laboratory practices. Each animal was subjected to general anesthesia and then a dorsal approach to the lumbar spine was performed. A complete laminectomy of the mid-lumbar vertebrae was performed, along with removal of the epidural fat, to expose the dura. A durotomy 8 having a length of about 4.5 millimeters was formed in the midline and cerebrospinal fluid leakage was visually confirmed, as illustrated in FIG. 1.

Figure 2:
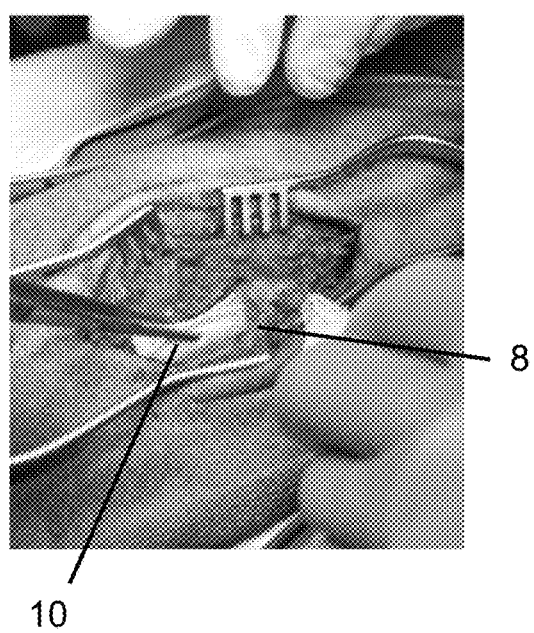
FIG. 2 is a photograph showing application of a durotomy sealant proximate the incision in the dura mater.
Figure 3:
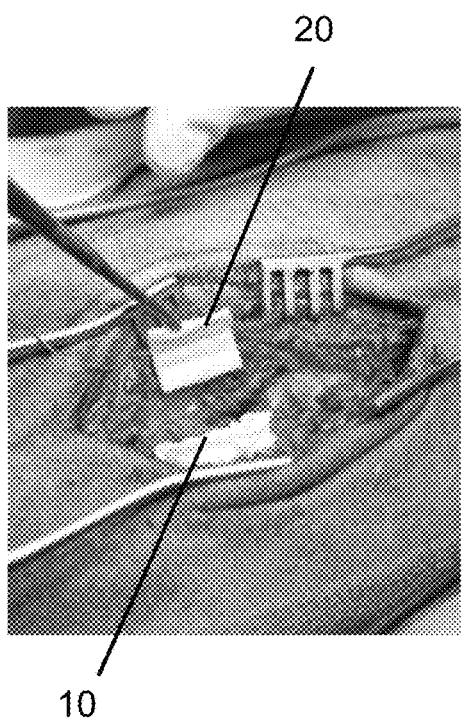
FIG. 3 is a photograph showing application of a pledget proximate the incision in the dura mater.
Figure 4:
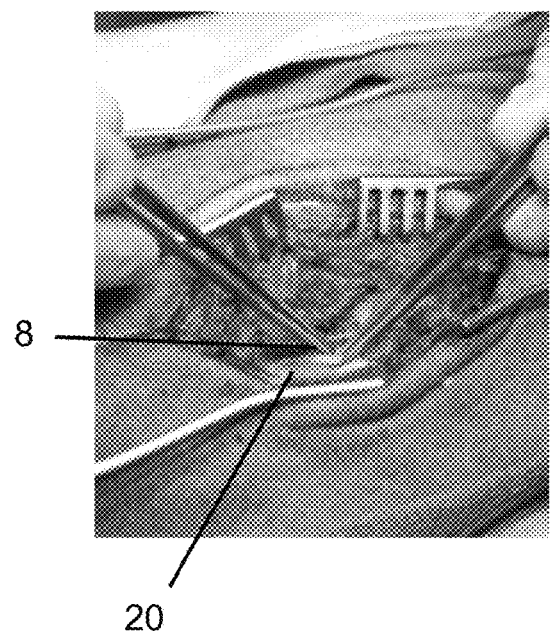
FIG. 4 is a photograph showing removal of the pledget from proximate the incision in the dura mater.
Figure 5:
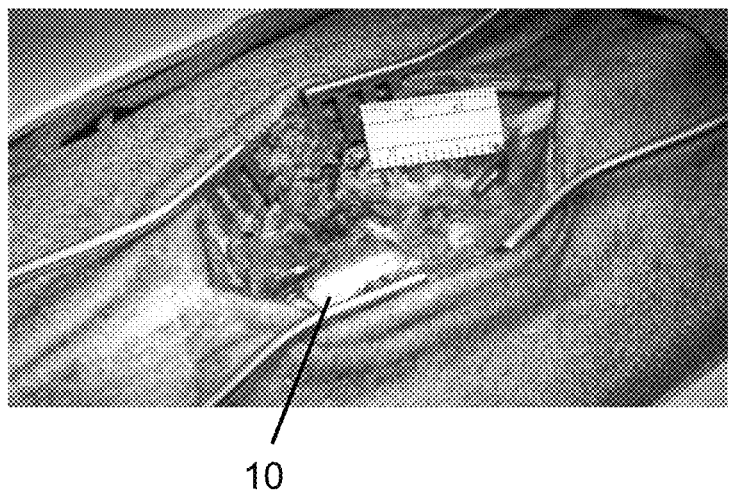
FIG. 5 is a photograph showing that the durotomy sealant formed a translucent covering over the incision in the dura mater.

A durotomy sealant dressing 10 that was prepared using the process in Example 1 was applied over the durotomy 8, as illustrated in FIG. 2. A cotton pledget 20 was then placed over the durotomy sealant dressing 10, as illustrated in FIG. 3. After 5 minutes observation, the pledget 20 was removed, as illustrated in FIG. 4, and the durotomy 8 was inspected for leakage of cerebrospinal fluid. The durotomy sealant dressing 10 formed a translucent seal over the durotomy 8, which allows the surgeon to work within the spinal column, as illustrated in FIG. 5.

If no leakage of cerebrospinal fluid was observed, a Valsalva maneuver was performed at a pressure of about 40 centimeters $H_2O$ for about 10 seconds. If cerebrospinal fluid leakage was observed, a second durotomy sealant dressing was applied in a similar manner and the procedure was repeated. If leakage continued, the durotomy sealant was removed and the durotomy was closed utilizing silk sutures.

The results of the durotomy sealant are set forth in Table 1. The durotomies of four of the five goats were sealed with no more than three durotomy sealant dressings. A fifth goat continued to leak cerebrospinal fluid with Valsalva maneuver following the second durotomy sealant dressing and required suture repair. It is believed that such leakage likely resulted from the misapplication of the durotomy sealant dressing or from the presence of residual epidural fat that interfered with the sealing process.

TABLE 1

| Animal | Cerebrospinal fluid leakage control with durotomy sealant dressing | Number of durotomy sealant dressings required to seal durotomy |
|---|---|---|
| 1 | Yes | 2 |
| 2 | No | n/a |
| 3 | Yes | 1 |
| 4 | Yes | 1 |
| 5 | Yes | 3 |

Figure 6:
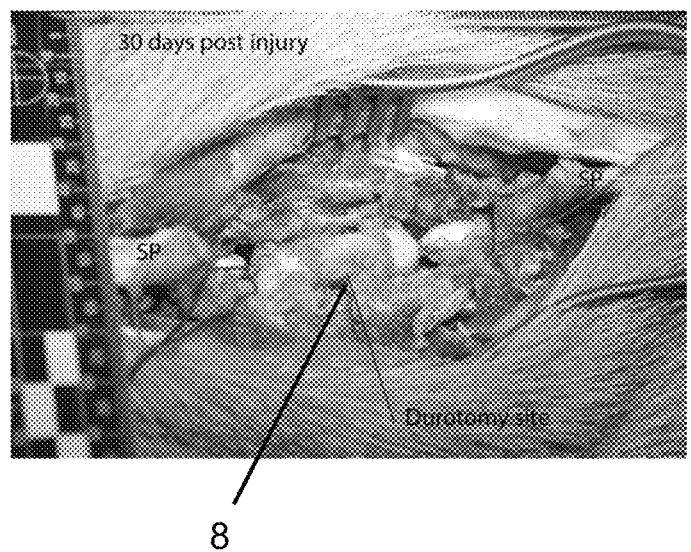
FIG. 6 is a photograph showing the durotomy site 30 days after the application of the durotomy sealant.

All of the goats survived the 30 day evaluation period during which none of the animals developed a wound infection. Thereafter, the animals were euthanized and the wound was reopened for inspection of the durotomy 8, as illustrated in FIG. 6. Based upon gross observation, all five goats developed normal fibrosis at the surgery site. None of the animals developed a pseudomeningocele.

Figure 7:
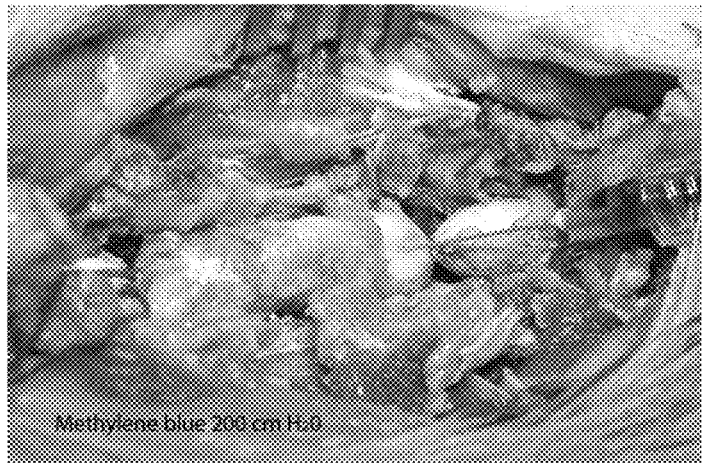
FIG. 7 is a photograph showing injection of methylene blue into the durotomy site without experiencing leakage.

Complete laminectomies were performed at the adjacent levels and the thecal sac was ligated using a #1 braided nylon suture. A needle having a diameter of about 25 gauge was introduced into the thecal sac and methylene blue was injected to a pressure of about 200 centimeters $H_2O$, as illustrated in FIG. 7. No leakage was observed at the durotomy site.

Based upon these results, it was concluded that the durotomy sealant dressing was highly effective as the durotomy sealant sealed 80% of the dural injuries initially and could not be dislodged with normal Valsalva pressures. The absence of a pseudomeningocele confirms that cerebrospinal fluid leakage did not occur after the surgical procedure.

In the preceding detailed description, reference is made to the accompanying drawings, which form a part hereof, and in which is shown by way of illustration specific embodiments in which the invention may be practiced. In this regard, directional terminology, such as "top," "bottom," "front," "back," "leading," "trailing," etc., is used with reference to the orientation of the Figure(s) being described. Because components of embodiments can be positioned in a number of different orientations, the directional terminology is used for purposes of illustration and is in no way limiting. It is to be understood that other embodiments may be utilized and structural or logical changes may be made without departing from the scope of the present invention. The preceding detailed description, therefore, is not to be taken in a limiting sense, and the scope of the present invention is defined by the appended claims.

It is contemplated that features disclosed in this application, as well as those described in the above applications incorporated by reference, can be mixed and matched to suit particular circumstances. Various other modifications and changes will be apparent to those of ordinary skill.

The invention claimed is:

1. A method of sealing a durotomy from which cerebrospinal fluid is leaking, wherein the method comprises:
   preparing a durotomy sealant dressing by applying an active agent to an electrospun dextran base, wherein the active agent comprises at least one of thrombin and fibrinogen;
   applying the durotomy sealant dressing to a durotomy;
   dissolving at least a portion of the durotomy sealant dressing; and
   sealing the durotomy with the dissolved durotomy sealant dressing to prevent cerebrospinal fluid from flowing through the durotomy without sutures.

2. The method of claim 1, further comprising applying pressure to the durotomy sealant dressing using a pledget when the durotomy sealant dressing is applied to the durotomy.

3. The method of claim 1, wherein the durotomy sealant dressing dissolves in less than about 4 minutes when the durotomy sealant dressing is applied to the durotomy.

4. The method of claim 1, wherein preparing the durotomy sealant dressing comprises:
   forming at least two layers that each comprise the active agent applied to the electrospun dextran base; and
   placing the layers adjacent to each other to form the durotomy sealant dressing.

5. The method of claim 1, further comprising applying a liquid to the durotomy sealant dressing while the durotomy sealant dressing is applied to the durotomy.

6. The method of claim 1, further comprising at least partially immersing the durotomy sealant dressing in a liquid before the durotomy sealant dressing is applied to the durotomy.

7. The method of claim 1, further comprising compressing the durotomy sealant dressing to modulate dissolving of the durotomy sealant dressing.

8. The method of claim 1, further comprising adding a diagnostic agent to the durotomy sealant dressing.

9. A method of sealing a durotomy from which cerebrospinal fluid is leaking, wherein the method comprises:
   preparing a durotomy sealant dressing by applying an effective amount of thrombin and an effective amount of fibrinogen to an electrospun dextran fiber base;
   applying the durotomy sealant dressing to a durotomy;
   dissolving at least a portion of the durotomy sealant dressing; and
   sealing the durotomy with the dissolved durotomy sealant dressing to prevent cerebrospinal fluid from flowing through the durotomy without sutures.

10. The method of claim 9, further comprising applying pressure to the durotomy sealant dressing using a pledget when the durotomy sealant dressing is applied to the durotomy.

11. The method of claim 9, wherein the durotomy sealant dressing dissolves in less than about 4 minutes when the durotomy sealant dressing is applied to the durotomy.

12. A method of sealing a durotomy from which cerebrospinal fluid is leaking, wherein the method comprises:
   preparing a durotomy sealant dressing by applying an active agent to an electrospun dextran base, wherein the active agent comprises at least one of thrombin and fibrinogen;
   applying the durotomy sealant dressing to a durotomy;
   applying a liquid to the durotomy sealant dressing;
   dissolving at least a portion of the durotomy sealant dressing; and
   sealing the durotomy with the dissolved durotomy sealant dressing to prevent cerebrospinal fluid from flowing through the durotomy without sutures.

13. The method of claim 12, further comprising applying pressure to the durotomy sealant dressing using a pledget when the durotomy sealant dressing is applied to the durotomy.

14. The method of claim 12, wherein the durotomy sealant dressing dissolves in less than about 4 minutes when the durotomy sealant dressing is applied to the durotomy.

15. The method of claim 12, wherein preparing the durotomy sealant dressing comprises:
   forming at least two layers that each comprise the active agent applied to the electrospun dextran base; and
   placing the layers adjacent to each other to form the durotomy sealant dressing.

\* \* \* \* \*